(12) United States Patent
Hummer (10) Patent No.: US 12,306,155 B2
(45) Date of Patent: *May 20, 2025

(54) DEVICES, SYSTEMS AND METHODS FOR DETECTING, MEASURING AND MONITORING CHEMICALS OR CHARACTERISTICS OF SUBSTANCES

(71) Applicant: Matthew Hummer, Atlantic Beach, FL (US)

(72) Inventor: Matthew Hummer, Atlantic Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/733,224

(22) Filed: Jun. 4, 2024

(65) Prior Publication Data

US 2024/0426797 A1 Dec. 26, 2024

Related U.S. Application Data

(63) Continuation of application No. 16/789,741, filed on Feb. 13, 2020, now Pat. No. 12,000,815.

(60) Provisional application No. 62/806,205, filed on Feb. 15, 2019, provisional application No. 62/879,610, filed on Jul. 29, 2019.

(51) Int. Cl.
 *G01N 33/00* (2006.01)

(52) U.S. Cl.
 CPC .................................. *G01N 33/00* (2013.01)

(58) Field of Classification Search
 CPC .............. G01N 33/00; G01N 33/0004; G01N 33/48707; G08B 21/12; G08B 21/20; G08B 27/006
 See application file for complete search history.

(56) References Cited

U.S. PATENT DOCUMENTS

| | | | | |
|---|---|---|---|---|
| 2004/0204915 A1* | 10/2004 | Steinthal | ................ | B82Y 30/00 702/30 |
| 2008/0262321 A1* | 10/2008 | Erad | ................ | G01N 35/00871 422/52 |
| 2021/0003461 A1* | 1/2021 | Tarkoma | ................ | G08C 23/00 |

* cited by examiner

*Primary Examiner* — Jennifer Wecker
*Assistant Examiner* — Jonathan Bortoli
(74) *Attorney, Agent, or Firm* — Lippes Mathias LLP (57) ABSTRACT

A system for measuring chemical concentrations and other attributes or conditions of the various forms of matter (solid, liquid or gas) in an environment. The system finds particular application for industrial processes and procedures whereby real-time, quasi-real-time or sampling chemicals of matter, or factors or conditions in an environment could help operations become more efficient, effective and sustainable.

16 Claims, 6 Drawing Sheets

DEVICES, SYSTEMS AND METHODS FOR DETECTING, MEASURING AND MONITORING CHEMICALS OR CHARACTERISTICS OF SUBSTANCES

CLAIM OF PRIORITY

This application claims priority from pending patent application Ser. No. 16/789,741 filed on Feb. 13, 2020, which in turn claims priority from Provisional Application Ser. No. 62/806,205 filed on Feb. 25, 2019 and 62/879,610 filed on Jul. 29, 2019.

FIELD

The present exemplary embodiment relates to devices, systems and methods for detecting, measuring or monitoring chemicals, biological material or other characteristics or conditions in various substances or the forms of matter.

BACKGROUND

Detecting the absence or presence of chemicals, biological material and other attributes or conditions along with quantifying associated levels in substances or across the various phases of matter (e.g. solid, liquid or gas) is of great need for many industries. Monitoring such chemicals or characteristics is especially helpful when part of a system or process of production.

SUMMARY

Devices, systems and methods are described for detecting, measuring or monitoring chemicals, biological substances (e.g. organism) or other characteristics in the various phases of matter. The present embodiment enables monitoring in continuous or quasi-continuous or sampling mode through a wide variety of monitor/detector mediums. The monitoring devices produce data and information that help optimize systems, allowing processes or procedures to become more efficient, cost-effective and sustainable.

In one aspect of the present embodiment, a method of detecting, measuring or monitoring chemicals, biological material or other characteristics or conditions using monitors/detectors or sensors includes detecting the presence or absence of at least one chemical, biological material or characteristic or condition; measuring levels or concentrations of chemicals, biological materials or characteristics or conditions; and monitoring levels of chemicals, biological materials or characteristics or conditions.

Data or information generated by the monitoring devices can be compared to threshold levels of data and an alert can be generated if the data collected by the monitoring device exceeds or is below the threshold levels. Other types of automated remedial actions such as robotics, software, autonomy or other means can be a result of comparing the data generated by the monitoring device to a threshold levels of data.

In another aspect of the present embodiment, a method of communication among monitoring devices or machine-to-machine communication is set forth, whereby sensors share data and information in order to optimize processes and procedures. Such data can include, but is not limited to, measurements or monitoring of characteristics or conditions such as location, temperature, humidity, moisture, vibration, pressure, light, pH, radiation, flow, motion, nutrient, barometer, force, biometric, infrared, Brix, chemical concentration, gas, biological material or sound. Methods of communication can include, but is not limited to, wireless telemetry that sends signals indicative of detected chemical or characteristic or condition of substances. The present exemplary method in which devices communicate with each other, creates a network of sensors spanning operations, which help to optimize processes and procedures.

In another aspect of the present embodiment, the monitoring devices communicate and transmit data and information to a distributed control system or computerized control system for a process or plant usually with many control loops, in which autonomous controllers are distributed throughout the system.

In another aspect of the present embodiment, the monitoring device comprising of monitor/detector component, factor controls, communication circuitry, and a power source operatively coupled to the monitor/detector component, factor controls and the communication circuitry for supplying power thereto, and wherein the communication circuitry is configured to transmit data to an associated receiver and wherein the monitor/detector component can include a plurality of monitors/detectors.

In another aspect of the present embodiment, one or more of the monitoring device elements or components such as communication circuitry, processor, memory, or power source is part of a printed circuit board that can be removed or replaced from the monitoring device.

In another aspect of the present embodiment, the printed circuit board comprising an antenna, a microcontroller and a voltammetry circuit. It should be appreciated that the printed circuit board can include a wide variety of additional components and elements as conventional and that any combination thereof can be printed on a carried material substrate. Methods of printing can include, but are not limited to, silk-screen, inkjet or other methods of electrophotography.

In another aspect of the present embodiment, one or more elements or components of the monitoring device can include a printed element or component.

In another aspect of the present embodiment, the sensor further comprising of active/passive induction devices (e.g. connectors, concentrators, cases, coatings, fans, filters, housings, micro-pumps, pressure fittings, pumps, valves, conduits, channels among other inducement mechanisms) for directing flow of air or liquid or other substance towards at least one of the monitor/detectors or away from at least one of the monitors/detectors. It should be appreciated that any number and any form of induction devices are envisioned and can be used.

In another aspect of the present embodiment, a sensor comprising a specific induction device in the form of a filter. It should be appreciated that any such filter can be used for filtering out biomolecules (e.g. microbial or macrobial) or other materials or substances that complicate detection or measurement or monitoring of chemicals, factors or characteristics or substances. One type of filter can include a nonporous membrane, which can self-assemble and form copolymers. Typically, nanopores membranes have a pore diameter between 1 and 100 nm and are well suited for separating or filtering nanoparticle sizes and shapes.

In another aspect of the present embodiment, a sensor comprises an induction device in the form of one or more housings, cases or coatings. The housings, cases or coatings can be removeable and replaceable and washable and reusable. The housings, cases or coatings can also be resistant to various factors in an environment including but not limited fluid, moisture, humidity, temperature, pH, corrosive chemicals, ionization, pressure, radiation, shock, stress, impact, explosion or other factors known to prompt failure in electronic or electrical components or create hazardous events. Housings and cases and coatings can be made from advanced materials, nano-materials or other durable or suitable substances. Specific types of coatings can be conformal, including acrylic, silicone, urethane, epoxy, parylene, fluorocarbon or nano-coatings among other suitable coatings.

In another aspect of the present embodiment, the monitoring device can include any number of housings, cases or coatings. It should be appreciated that the method of deploying such housings, cases and coatings will be determined by the environment in which the sensor is deployed. For example, hazardous environments such as extreme temperature or explosion-prone areas have industrial standards that were designed to support the wide range of process-industry applications.

In another aspect of the present embodiment, the monitoring device or sensor or monitoring system includes a display.

In another aspect of the present embodiment, the sensor comprises a case or housing that is selectively attachable to a receiver or data processor or case of a receiver. A receiver can include a smartphone, personal communication device, implantable, wearable, textile, or peripheral device associated with an electronic communication device.

In another aspect of the present embodiment, the monitor/detector component comprises a single monitor/detector or a plurality of detectors of various forms. The detectors can be individually replaceable or can be replaced as a unit. The monitor/detector component or monitor/detector is operatively coupled to the printed circuit board or associated elements or components through any means necessary, including various connectors, cases or housings that join the monitor/detector with the printed circuit board or other components or elements of the monitoring device.

In another aspect of the present embodiment, wherein the power source of the monitoring device can be active or passive and include an antenna configured to receive energy wirelessly and supply the received energy to at least one of the detector components and communication circuitry.

In another aspect of the present embodiment, the monitor/detector or monitor/detector component can be a removeable/replaceable unit or test consumable cartridge. The cartridge comprises at least one of a monitor/detector component, monitor/detector, a reference matter, diluent matter, calibration matter, mixing matter, mixer, reservoir, active/passive induction (e.g. connector, case, flow conduit, filter, fitting, housing, pump, valve, etc.) for operatively coupling the cartridge to the monitoring device, while maintaining appropriate conductions (e.g. pressure levels, temperature, etc.).

In another aspect of the present embodiment, a monitoring system comprises monitoring device, measurement hardware, power source, communication circuitry, factor control, reservoirs, induction devices (e.g. housings, coatings, cases, connectors, pressure fittings, etc.).

In another aspect of the present embodiment, the monitoring system further comprises at least one of durable transmitter or associated receiver. The durable transmitter can include an inlet that can have active/passive induction devices/components (e.g. flow conduits, pump, purge, valves etc.), factor controls, measurement hardware along with communication circuitry and active/passive power source. The transmitter can include any type of component as conventional that moves measurement data from its source to a process control system otherwise defined as an associated receiver. The system can be configured to communicate with an associated receiver, which can be in the form of a personal communication device, hand-held electronic device, implantable, wearable, textile, remote data terminal, peripheral device or distributed control system among other suitable receivers.

In another aspect of the present embodiment, matter can be used for one or more of changing conductivity, dilution, flow, flush, rinse, cleanse, sterilize among other requirements for accurately detecting, measuring or monitoring chemicals or characteristics of substances.

In another aspect of the present embodiment, solids can be liquified and become one of diluted, flowed or flushed through the sensor or monitoring device.

In another aspect of the present embodiment, the sensor or monitoring device can be placed inside or outside of the area, which is the source of the chemical, biological material, factor or characteristic or substance to be detected, measured or monitored.

In another aspect of the present embodiment, the sensor or monitoring device can be partially or entirely submerged in a substance or floating in a substance or part of a flow conduit transporting or storing a substance or embedded in an enclosed area or embedded in a lining or covering or wrapping of an enclosed area or embedded or attached to infrastructure or equipment that interacts with the environment of a substance.

In another aspect of the present embodiment, a monitor/detector is calibrated, which includes obtaining a minimum chemical concentration value and a maximum chemical concentration value of reference solutions. After the calibration process using reference solutions, the chemical concentration of a process solution is measured whereby the process solution can be diluted by the same factor as the reference solution. A calculation using the dilution factor of the solutions is performed to obtain an estimated chemical concentration of the process solution.

In another aspect of the present embodiment, a monitor/detector is calibrated such that the monitor/detector consistently returns accurate or stable measurements. Such calibration process may require more than one reading of data generated by the monitor/detector. The monitor/detector can be calibrated by diluting a reference solution by the same amount or factor as a process solution to create a linear range with a maximum value and a minimum value.

DETAILED DESCRIPTION

The present exemplary embodiment is devices, systems and methods of detecting, measuring or monitoring chemicals, analytes, factors or characteristics in various substances or phases of matter. All illustrations of the drawings are for the purpose of describing selected versions of the present invention and are not intended to limit the scope of the present invention. The present exemplary embodiment can have a wide variety of uses, which includes, but not limited to industrial process applications.

Figure 1:
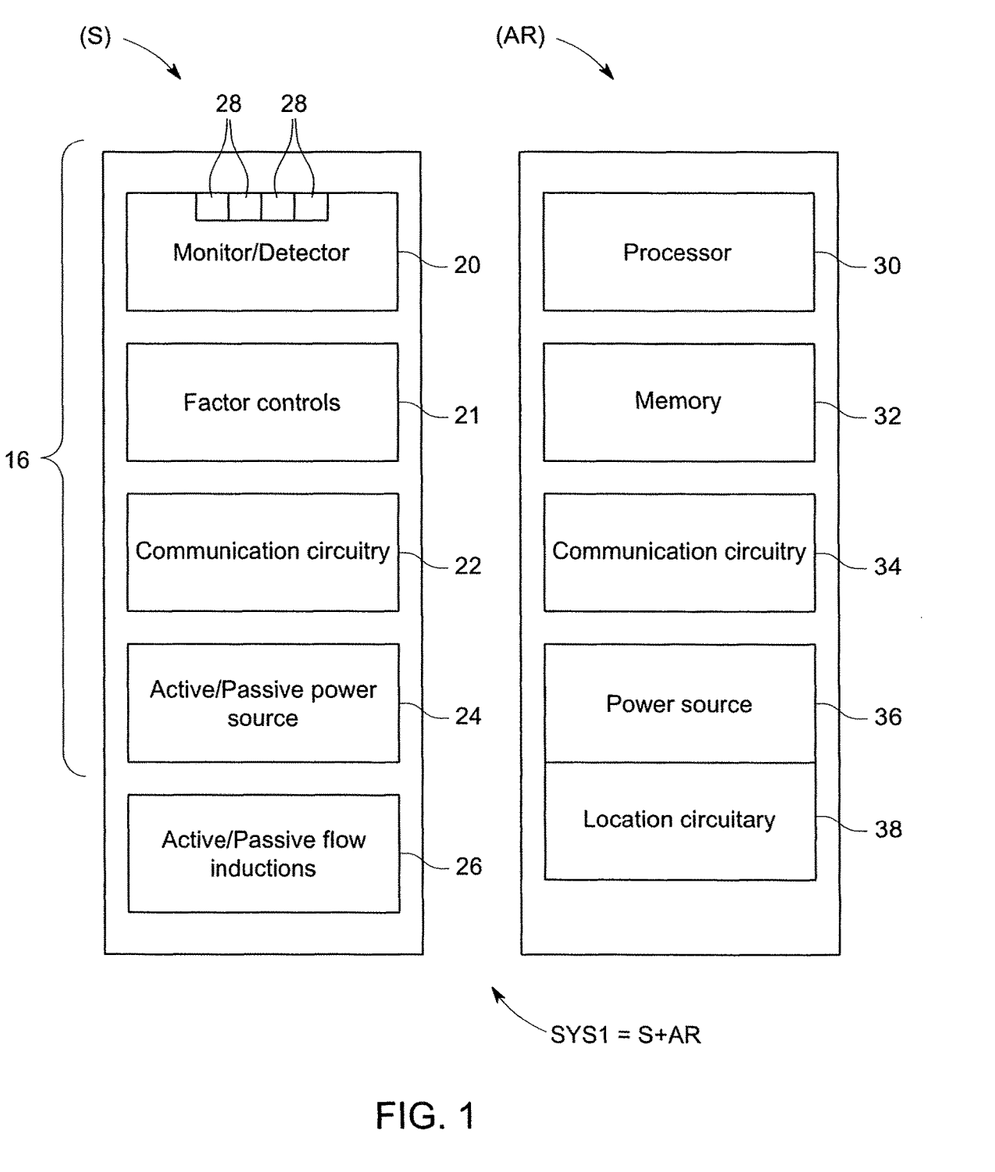
FIG. 1 illustrates a schematic diagram of a first exemplary system.

With reference to FIG. 1, an exemplary first system for detecting, measuring or monitoring chemicals, attributes or characteristics is illustrated and identified generally as (SYS1). The first system (SYS1) comprising sensor(S) and associated receiver (AR). In this exemplary embodiment, the sensor includes one or more of a monitoring device (16), which can include at least one of a monitor/detector component (20), factor control (21), communication circuitry (22) and power sources (24).

In the present embodiment, the factor controls (21) may be necessary given specific operational requirements or conditions (e.g. temperature, pH, humidity, moisture, light, among other compositional or environmental factors) for a particular monitor/detector (20). The factor controls (21) manage compositional and environmental factors and conditions necessary for proper functionality of the monitor/detector (20) and can include such elements or components like pH balancers, humidity controls, moisture controls, temperature controls, viscosity controls, aeration controls, flow controls, acetate controls, acidity control, respiratory controls, composition control, concentration control among other types of controls.

One monitor/detector component that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector elements or components can also be used in accordance with the present disclosure. At least one of the sensors (28) can be configured for generating a signal which is indicative of aeration, acetate, acidity, acceleration, chemical concentration, product concentration, location, temperature, humidity, moisture, vibration, pressure, mass, distance, speed, optical, light, pH, radiation, flow, motion, imagery, nutrient, barometer, force, biometric, infrared, sound, respiratory, yield, viscosity, velocity, uptake, transfer, evolution, oxygenation, demand among other attributes or conditions in an environment or related control systems or control strategies for industrial systems or processes.

Types of monitors/detectors (20) can include, but are not limited to: electrochemical, microelectrochemical systems (MEMS), nanoelectromechanical systems (NEMS), various gas sensors, various fluid sensors, metal oxide semiconductor, zinc oxide, redox electrode, potentiometric, amperometic, aptamer, pellistor, microwave chemistry, electronic nose, electronic tongue, infrared, thermal, photoionization (PID), chromatography, micro gas chromatography, surface acoustic wave (SAW), chemoresistors, field-effect transistor (FET), optical, laser, biosensor or among other micro, macro, meso or nano sensors.

Monitors/detectors (20) can include a wide variety of additional components or elements as conventional or necessary including, but not limited to various antenna, various sensors, microcontrollers, voltammetry circuits or other circuits. An exemplary microcontroller can include various sub-components or sub-elements such as a processor in the form of a central processing unit, communication circuitry in the form of Bluetooth low energy or similar method of wireless communication, analogue to digital converter and a serial peripheral interface. The microcontroller can be operatively coupled to the voltammetry circuit through the analogue to digital converter and a serial peripheral interface. The voltammetry circuit can include sub-components and sub-elements such as a data acquisition system, and various potentiostatic control circuits for any number of electrodes or detectors.

The monitoring device (16) further comprises communication circuitry (22) and an active/passive power source (24). The communication circuitry (22), in one embodiment, includes at least one of a near field communication device, Bluetooth communication device, WIFI communication device, or any other suitable communication circuitry for establishing communications with the associated receiver (AR). The power source (24) can be an active power supply such as a battery (lithium or other) mounted, printed or otherwise contained within the monitoring device (16). In other embodiments, the power source (24) can be passive such as an antenna configured to receive energy wirelessly and supply the received energy to one or more of the monitor/detector components (20), communication circuitry (22) or factor controls (21) such that no onboard battery is required for operation of the monitor device (16). In other arrangements, the power source (24) can be a connector configured to couple with a port of an associated receiver (AR) (e.g. smartphone, wearable, implantable, tablet, textile, peripheral devices etc.) to receive power from a power source of the associated receiver (AR).

In another embodiment, one or more elements or components of the monitoring device (16) or sensor(S) can include a printed element or component. Such fabrication methods can include but are not limited to ink-jet or silk-screen printing or other methods of printing and additive manufacturing.

Active or passive flow induction devices (26) can be provided for ensuring adequate and continuous flow of matter (e.g. air, liquid, gas or other substances) to the monitors/detectors (20). Such devices can include fans, filters, pumps, purges, valves, louvers, vents, channels, conduits, compressors, connectors, cases, coatings, housings or any other type of element or component that actively or passively induces the flow of matter. Induction devices can be separately replaceable within the device or system and can include their own power supply. Alternatively, an active induction device can be configured to receive power from the power supply (24).

An induction device that is particularly applicable to the present embodiment includes a filter. The filter can be of any variety capable of filtering out biomolecules and other material that complicate detection, measurement or monitoring of chemicals, analytes, factors or substances. One such filter includes a nanoporous membrane, which can self-assemble and form copolymers or polymers capable of filtering microbial and macrobial or various sized particles.

It should be appreciated that the monitor/detector component (20) can comprise a plurality of sensors (28). The sensors (28) can be individually replaceable or can be replaced as a unit. Replacement of the sensors may be necessary due to sensor degradation. In other situations, a user may wish to detect certain chemicals, factors or substances and will choose which sensors to install in the system. In one embodiment, the entire monitor device (16) is replaceable as a unit.

The sensors (28) may detect a wide array of attributes or characteristics including but not limited to: chemicals, analytes, gases, biological material and various other substances, attributes or conditions of an environment such as aeration, acetate, acceleration, Brix, chemical concentration, product concentration, location, temperature, humidity, moisture, vibration, pressure, mass, distance, speed, optical, light, pH, radiation, flow, motion, imagery, nutrient, barometer, force, biometric, infrared, sound, respiratory, yield, viscosity, velocity, uptake, oxygenation, transfer, evolution, demand among other attributes or conditions in an environment.

It will be appreciated that the monitoring device (16) is configured to communicate with the associated receiver (AR). That is, the monitoring device (16) collects data and transmits or otherwise shares the collected data with the associated receiver (AR) for further processing. The associated receiver (AR) of the illustrated embodiment includes processors (30), memory (32), communication circuitry (34), and power sources (36). It will be appreciated that the associated receiver (AR) can include a wide variety of additional components as is conventional or required by the sensors (28). Such additional components can include display devices, input devices, output devices, peripheral devices, various sensors, various circuitries (e.g. location) and various antennas etc.

Data collected by the monitor/detector components (20) can be transmitted via communication circuitry (22) of the monitoring device (16) to communication circuitry (34) of the associated receiver (AR). Other data, such as sensor state, status, performance data, power level or other factors in an environment and the like can also be transmitted to the associated receiver (AR). Any suitable manner of transmitting the data from the monitoring device (16) or sensor(S) to the associated receiver (AR) can be employed.

The data collected and transmitted by the monitoring device (16) or sensor(S) can then be processed by the associated receiver (AR) to detect, measure or monitor one or more chemicals, attributes or characteristics in accordance with the present disclosure or one or more methods set forth in U.S. Pat. No. 8,629,770 to Hummer et al. and U.S. Pat. No. 7,176,793 to Hummer. To this end, suitable software for analyzing the data is stored in memory (32) of the associated receiver (AR). Other detection and/or analyzing methods and techniques may also be used in conjunction with aspects of the present disclosure or as suitable for a specific type of monitor/detector component (20) or sensors (28).

In one embodiment, the software stored in memory (32) can be in the form of an application, or "app", that is downloaded from an app store or the like. The app can be provided with various "signatures" of chemicals or data or information related to other attributes or characteristics in an environment. The signatures, data or information of the app can be compared to the data collected by the monitoring device (16). The app can be configured to be automatically updated with new signatures or data related to factors or conditions as the need to detect particular chemicals or factors arise. That is, it is possible to provide new and/or additional chemical signatures or conditions or attributes for the app to check against the data to detect specific chemicals or attributes.

The app can further include features such as adjustable thresholds. For example, for some chemicals, analytes, factors or substances that are routinely present in certain amounts or levels and/or not generally considered dangerous or unwanted below certain levels, the application can be configured to detect or trigger an alarm when a threshold amount is met or exceeded or below. For some chemicals, attributes or substances which are considered dangerous or unwanted in any amount, the thresholds would not generally be adjustable.

The app can be further configured to, once a chemical or factor or substance is detected, share the detection data or information. For example, the application can be configured to use the communication circuitry (34) to broadcast an alert (or generate a notification) via any suitable communications network (e.g., WIFI, NFC, Bluetooth, cell, etc.). The alert may be directly sent to other receivers (e.g. smartphones or personal communication devices in the area) or may be sent to a server (or through a network) and then on to devices within a range of a given location. Accordingly, the application can be configured to use location information from a GPS chip, various location circuitry, WIFI or any other location information available to the associated receiver (AR) to identify the location of the detected chemical, attribute or characteristic of the substance. The app can be configured to communicate with a distributed control system (e.g. autonomous or semi-autonomous) or alert personnel or authorities in the event unwanted chemicals, factors or substances are detected.

Providing the monitoring system (16) or sensor(S) in a separate component that can be remotely deployed or attachable to a smartphone, other personal communication device or associated receiver (AR) or case of an associated receiver has several advantages. For example, any and all such devices can become sensors upon the provision of suitable induction devices (26) such as housings, connectors, coatings or other elements or components necessary for proper functionality. In one embodiment, housings, cases and coatings, are used to protect the monitoring system or sensor from various factors in an environment. Such factors can include, but are not limited to fluid, moisture, humidity, temperature, pH, corrosive chemicals, ionization, pressure, radiation, shock, stress, impact, explosion or other factors known to prompt failure in electronic or electrical components or create hazardous events. A monitoring system for use with mobile communication device is disclosed in U.S. Pat. No. 9,922,525 to Hummer et al., which is incorporated herein by reference to its entireties.

Figure 2A:
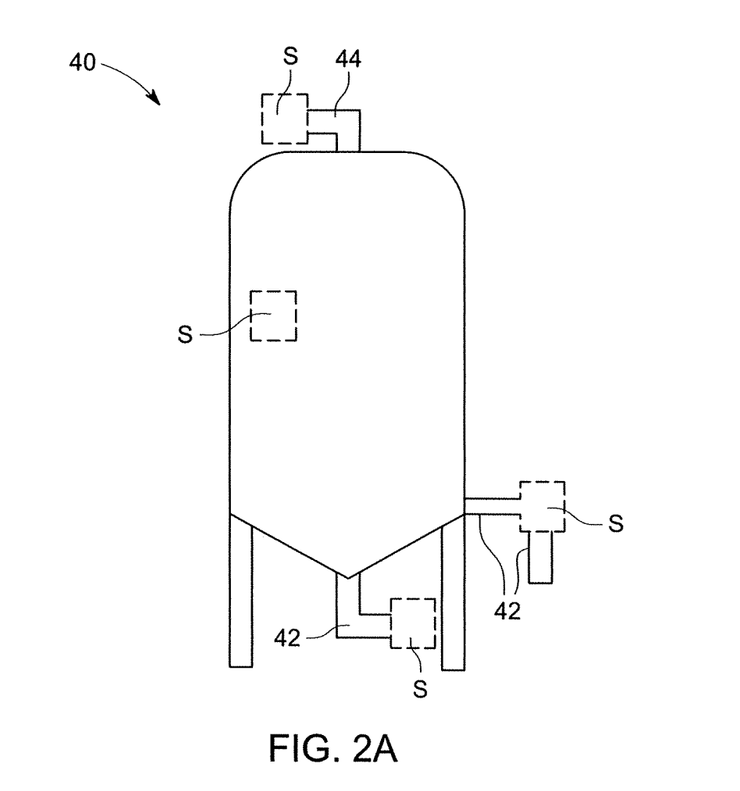
FIG. 2A illustrates exemplary enclosed area in the form of a tank.
Figure 2B:
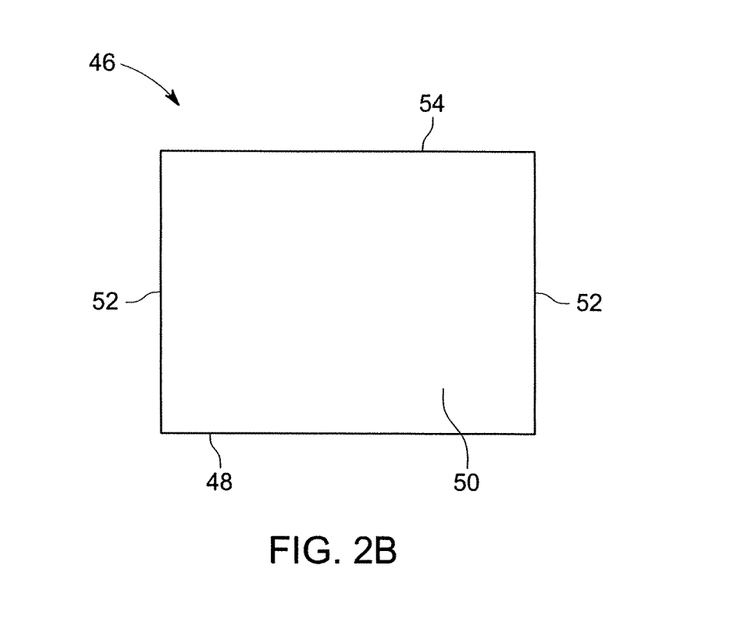
FIG. 2B illustrates exemplary enclosed area in the form of a container.

For example, with reference to FIGS. 2A and 2B, a monitoring device (16) or sensor(S) is provided in a separate enclosed area or semi-enclosed area (40), such as a tank or container or the like. FIG. 2A illustrates the monitoring device (16) or sensor(S) or system (SYS1) placed inside of the area for detecting, measuring or monitoring chemicals, attributes or characteristics such as a tank, for example. In other embodiments, the monitoring device (16) or sensor(S) or system (SYS1) can additionally or alternatively monitor or measure chemicals or other factors outside of the area (40).

In one embodiment, the monitoring device (16) or sensor (S) or system (SYS1) can be stationary within the area (40) or mobile within the area (40). In another embodiment, the monitoring device (16) or sensor(S) or system (SYS1) can have a density equal to or less than a density of the matter being monitored or measured within the area (40), such that the device or system can be floating. In another embodiment, the monitoring device (16) or sensor(S) or system (SYS1) can be tied to the area (40) such that the system has a limited range of motion using a coiled tethered connection line, or the like. The coiled tethered connection line provides bobbing flexibility and movement within a refined area. This design also features a larger surface area (e.g., extending a longer distance vertically above and below and horizontally on either side of the device or sensor or system), allowing for detection of chemicals and other characteristics of the areas that extend above and below and either side of the floating or tethered device. The exemplary embodiment can also have a built-in display for immediate reading of data. Like other embodiments, this example also connects and transmits data to remote associated receivers (AR) for further analysis that incorporates data from other sensors or systems deployed throughout various networks, systems or facilities.

In another embodiment, the monitoring device (16) or sensor(S) or system (SYS1) can be attached or embedded in any side or wall of the enclosed or semi-enclosed area (40) such as tank or container. Another method of deployment can include attaching or embedding the sensor in a lining or wrapping of an area (40). In other embodiments, the device (16) or sensor(S) or system (SYS1) can be attached or embedded in infrastructure or equipment or an independent mount (44) located inside or outside of the area (40).

In other embodiments, the monitoring device (16) or sensor(S) or system (SYS1) can be placed outside of an area (40) such as a tank or container to detect, measure or monitor chemicals or characteristics of substances emanating from inside of the area (40). It should be appreciated that any method suitable for deploying the monitoring device or sensor or system inside or outside of an area (40) such as tank or container shall be considered in the present embodiment. One such method of sensor deployment outside of an area (40), includes attaching or embedding the device or sensor or system in one or more flow conduits (42) extending from the area (40) such as a tank or container. The flow conduits can exit the interior of the area (40) from any location of the tank (e.g. top, side or bottom).

It should be appreciated and understood that the device or sensor or system can have various types of arrangements of active/passive flow inductions, such that flowable matter is directed towards the monitor/detector (20) for detection, measuring or monitoring and away from the monitor/detector (20) after detection, measuring or monitoring has occurred. For example, the monitoring device can be placed in an enclosed area or chamber, whereby various active/passive induction devices such as flow conduits, filters, cases, connectors, coatings, seals etc. help direct various types of matter to the chamber for measuring or monitoring and away from the chamber after measuring or monitoring has taken place. It should be appreciated, that a wide variety of methods for deploying devices, sensors or systems is envisioned, such that the matter to be measured or monitored is directed to the monitor/detector for measuring or monitoring and flushed away from the monitor/detector after measuring or monitoring has taken place.

The monitoring device (16) or sensor(S) or first exemplary system (SYS1) can be configured to communicate with other devices besides (or in addition to) the associated receiver (AR). Such devices can include transmitters, scanners or other devices adapted to connect and receive data from a plurality of such monitoring devices or sensors disposed in a plurality of respective enclosed or semi-enclosed areas such as tanks or containers or the like.

In one example, a scanning device or like device can be associated with a conveyor or like system for scanning enclosed areas such as containers or packages or the like by communicating with monitoring devices associated with the packages as they advance through a process. In another example, the monitoring devices of the present disclosure can be associated with forms of matter (e.g. solids, liquids or gases) not in a package per se, but rather involved in an industrial process, whereby the industrial process stores or transports the various forms of matter. It will be appreciated that a wide variety of applications for the technology of the present disclosure are contemplated.

In some embodiments, it can be advantageous to include one or more active or passive flow inducing devices or components (26) for ensuring sufficient flow of substance across the monitor/detector component (20). This can be particularly advantageous for applications wherein the sensors are stationary or in a fixed location and flow induction is necessary for proper functionality of the monitor/detector component. Suitable devices can include concentrators, fans, vacuums or pumps or flow conduits, coatings or the like for displacing the various forms of matter across and/or adjacent a sensor installation. In some applications, housings, cases, coatings, louvers or vent openings or the like can be positioned to maximize flow to the sensor. Increasing flow can make detection, measuring or monitoring of certain materials or characteristics more efficient and effective.

It should be appreciated that any number of sensors or monitoring devices in any number of areas, with any type of arrangement can be deployed such that the data collected and reported can be representative of the matter to be measured or monitored in an area or process. In one aspect of the present embodiment, spatial arrangement of the sensors or monitoring devices can be an important factor when measuring or monitoring chemicals, factors or other substances across a wide area or lengthy process.

With reference to FIG. 2B, an enclosed area (46) in the form of a container is illustrated. The container can be of any size, shape or material including large containers and tanks used for industrial processes (e.g. storage, transmission and transportation) and small containers and packaging used for products like food, beverage, drug and other types of consumables or consumer goods. Such containers are often enclosed, however it should be appreciated that the exemplary container can be partially enclosed or include doors or latches or other mechanisms or materials that open and close or can be removed. The exemplary container comprises of a bottom (48) with a pair of opposing, upstanding similar sides (50) and a pair of similar opposing ends (52), and a top (54) for covering and closing the container. It should be appreciated that the top can comprise of various forms such as lids, caps, covers, wraps among other types of coverings made of various materials.

Depending on the size of the container (46), one or monitoring devices (16) or one more sensors(S) are placed within the container to detect harmful or unwanted materials such as chemicals, analytes, biological materials, gases, or characteristics or conditions of the area. Other such devices and methods for detecting, measuring and monitoring contents in a container are disclosed in U.S. Pat. No. 7,176,793 to Hummer et al. and U.S. Pat. No. 7,667,593 to Hummer and U.S. Pat. Nos. 7,911,336 to 8,674,827 to Hummer and U.S. Pat. No. 8,629,770 to Hummer, which all hereby incorporated herein in their entireties.

Figure 3:
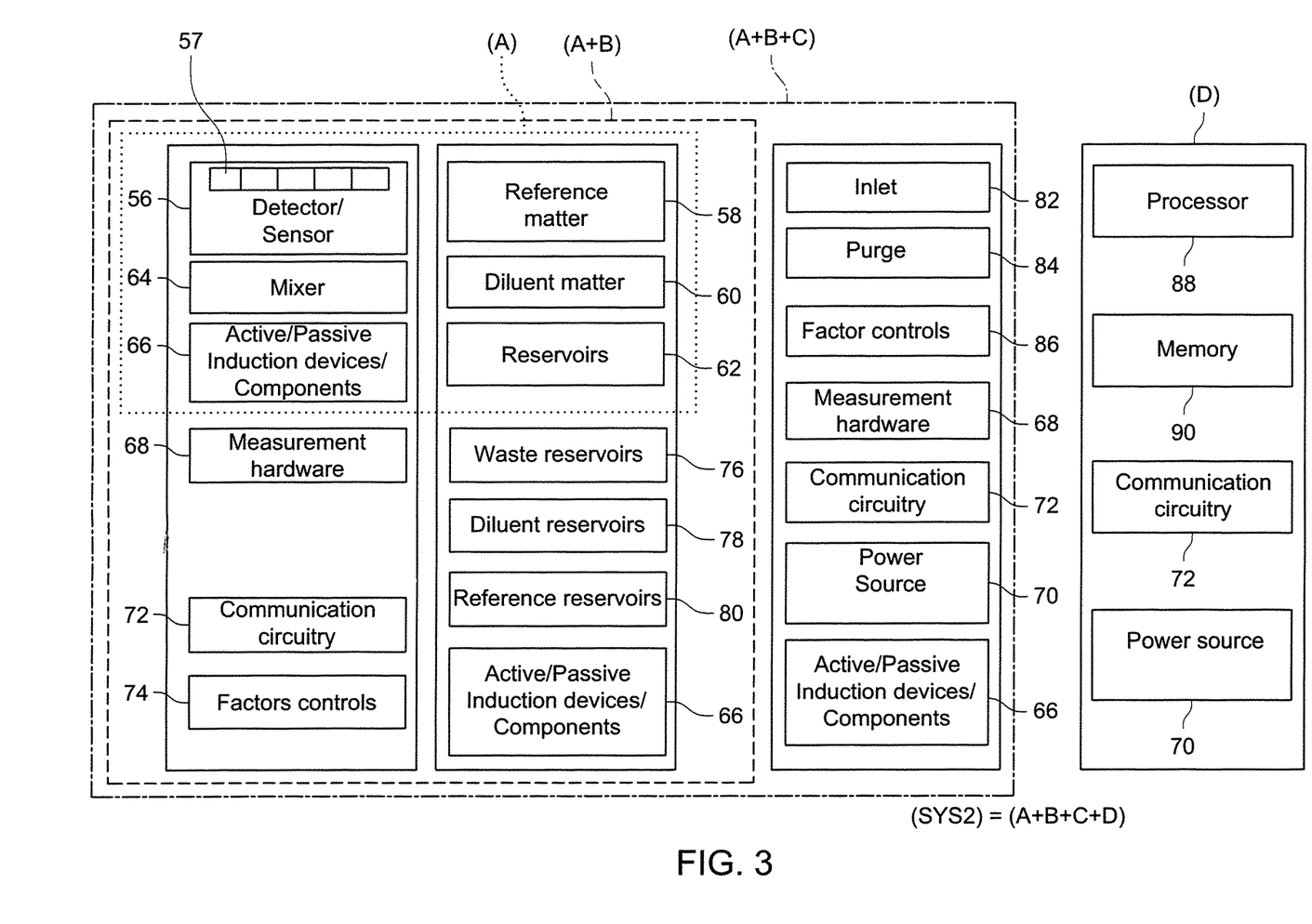
FIG. 3 illustrates a schematic diagram of a second exemplary system.

With reference to FIG. 3, an exemplary second system for detecting, measuring or monitoring chemicals, attributes or characteristics in an environment is illustrated and identified generally as (SYS2). The second system (SYS2) comprising four separate major components each having their own sub-components. The first major component is a removable/replaceable cartridge (A). The second major component is the system for chemical detection (A+B), which can include the removable/replaceable cartridge (A). The third major component is the durable transmitter (C) and the fourth major component is the associated receiver (D). All together the four major components (A+B+C+D) make-up the second exemplary system detecting, measuring or monitoring chemicals, attributes or characteristics (SYS2).

It should also be appreciated that the second exemplary system (SYS2) can also be designed without a removable/replaceable cartridge (A), in which case the components of the cartridge (A) would be built into either of the system for chemical detection (A+B) or the durable transmitter (C) or separate component.

In one embodiment, the removable/replaceable cartridge (A) comprising at least one of a detector/sensor component (56), a reference matter (58), a calibration matter or diluent matter (60), various reservoirs (62) (e.g. waste, diluent or reference), a mixer (64) or various active/passive induction devices or components (66). The detector/sensor component (56) can include a plurality of detectors or sensors (57) and the mixer is used to uniformly combine various forms of matter such as solids, liquids or gases or other substances. The induction devices/components (66) (e.g. flow conduits, filters, valves, pump, purge, connectors, compressors, coatings, housings, casings etc.) help to move flowable materials throughout the system, while maintaining appropriate conditions such as pressure, temperature, pH level, humidity among other controllable factors within the second exemplary system (SYS2).

In another embodiment, whereby the system (SYS2) does not include a cartridge (A), various approaches can be employed for sustaining forms of matter in the system (SYS2). For example, reference matter (58) and diluent matter (60) in various sized containers or reservoirs can flow into the system (SYS2) as needed.

It should be appreciated that the detectors/sensors (56) can comprise a plurality of sensors (57). The sensors (57) can be individually replaceable or can be replaced as a unit. Replacement of the sensors may be desired due to sensor degradation. In other situations, a user may wish to detect certain chemicals or attributes or conditions and will choose the appropriate sensors to install in the second exemplary system (SYS2).

The sensors (57) may detect a wide array of factors or characteristics including but not limited to: chemicals, analytes, gases, biological material and various other substances, attributes or conditions such as aeration, acetate, acceleration, Brix, chemical concentration, product concentration, location, temperature, humidity, moisture, vibration, pressure, mass, distance, speed, optical, light, pH, radiation, flow, motion, imagery, nutrient, barometer, force, biometric, infrared, sound, respiratory, yield, viscosity, velocity, uptake, oxygenation, transfer, evolution, demand among other attributes or conditions.

In addition to containing the components of the removable/replaceable cartridge (A), the system for chemical detection, measuring or monitoring (A+B) can also include one or more of the following components or elements: a measurement hardware (68), an active/passive power source (70), communication circuitry (72), factor controls (74) (e.g. thermal plate, pH balancer, humidity control etc.), and various active or passive induction devices or components (66) such as conduits, connectors, concentrators, compressors, fans, filters, pumps, vents, valves, coatings, channels among other flow inducement or flow regulation or pressure regulation mechanisms for aiding the movement of flowable material.

The system for chemical detection (A+B) can also include other elements and components such as waste reservoirs (76), diluent reservoirs (78), reference reservoirs (80) and active/passive induction devices or components (66) for moving flowable material throughout the system (SYS2). The elements and components can be designed to be included in the removable/replaceable cartridge (A) or the system for chemical detection (A+B) or the durable transmitter (C) or other components.

The third component, a durable transmitter (C) can include: an inlet (82), a purge (84), various factor controls (86), measurement hardware (68) along with communication circuitry (72), a power source (70) and various active/passive induction devices or components (66). The transmitter (C) can include any type of component that moves data from its source to a process control system otherwise defined as an associated receiver (D).

In another embodiment, one or more elements or components of the removeable replaceable cartridge (A) or system for chemical detection (A+B) or durable transmitter (C) can include a printed element or component. Such fabrication methods can include but are not limited to ink-jet or silk-screen printing or other methods of printing and additive manufacturing.

It will be appreciated that the three components (A+B+C) can be configured to communicate with a receiver (D). The receiver (D) can be in the form of a personal communication device, hand-held electronic device, remote data terminal, peripheral device, distributed control system among other suitable receivers.

The receiver (D) of the illustrated embodiment includes a processor (88), memory (90), communication circuitry (72), and a power source (70). It will be appreciated that the associated receiver (D) can include a wide variety of additional components as is conventional. Such additional components can include display devices, input devices, output devices, various sensors, various antennas and other peripheral devices.

Data collected by the system components (A+B+C) is transmitted via communication circuitry (72) of (A+B+C) to communication circuitry (72) of the associated receiver (D). Other data, such as sensor state, status, power, performance, temperature, humidity, pH level, brix, nutrient availability among other attributes, conditions and the like can also be transmitted to the associated receiver (D). Any suitable manner of transmitting the data from the three major components (A+B+C) to the associated receiver (D) can be employed including wireless or wired transmission.

Chemical detection and measurement methods can be in accordance with one or more methods set forth in U.S. Pat. No. 8,629,770 to Hummer et al. and U.S. Pat. No. 7,176,793 to Hummer to U.S. Pat. No. 9,922,525 Hummer. To this end, suitable software for analyzing the data can be stored in memory (90) of the associated receiver (D). Such software can also be a part of the measurement hardware (68) of (A+B) or (A+B+C) allowing so called "edge computing and analysis". In such a case, relying on an external receiver may not be necessary for basic computing and decision making. However, other detection and/or analyzing methods and techniques may be used in conjunction with aspects of the present disclosure.

In one embodiment, the software stored in memory of the associated receiver (D) can be in the form of an application, or "app", that is custom built or downloaded from an app store or the like. The app can be provided with various "signatures" of chemicals or data related to other attributes or conditions. The signatures or data related to attributes or conditions can be compared to the data generated by the system to determine whether the chemical signature or data related to factors or conditions were detected (present or absent) by the system (A+B+C). It should be appreciated that such software can also run directly on the measurement hardware of (A+B), (A+B+C) or (A+B+C+D).

The app can be configured to be automatically updated with new chemical signatures or attributes or conditions as the need to detect particular chemicals, attributes or conditions arise. That is, it is possible to provide new and/or additional chemical signatures or characterizations of attributes or conditions for the app to check against the data to detect specific chemicals or attributes or conditions. Similarly, software stored on measurement hardware (68) of (A+B), (A+B+C) and (A+B+C+D) can also be remotely updated.

The application software (app) can further include features such as adjustable thresholds of chemical concentrations, attributes or conditions. The app can also include analytics helpful in predicting certain operating conditions or control strategies that have high probability of producing specific outputs. For example, based on specific measurements of chemical concentrations, attributes or characteristics a plant or factory can predict specific outcomes as well as resource requirements for its operational assets. This method of operating is deemed a control system design or control strategy of which the present invention provides critical input data.

The app can be further integrated with a distributed control system otherwise known as an autonomous or semi-autonomous system for managing processes and factory-wide systems. For example, the application can be configured to use the communication circuitry (72) of the associated receiver (D) to broadcast an alert (or generate a notification) via any suitable wired or wireless communications network (e.g., WIFI, NFC, Bluetooth, cell, etc.). The alert may be directly sent to workstations and personal communication devices of personnel in the area or may be sent to a server (or through a network) and then on to devices within a range of a given location. Data and information may also be fed to a semi-autonomous or autonomous operating system. Accordingly, the application can be configured to use location information from a GPS chip, WIFI or any other location information available to the associated receiver (D) to identify the location of the detected chemical.

The app can be configured to alert appropriate personnel or authority in the event certain chemicals, factors or precursors to unwanted events such as contamination, explosion or fire among other unwanted incidents are detected. For example, alerts can be triggered when a specified threshold of highly toxicity, contamination, explosive or unwanted chemical or environmental factor is exceeded. Furthermore, in situations for monitoring for foodborne illness from toxins and contamination, data collected from the many networked systems (SYS2) can be shared with appropriate personnel such as regulators, inspectors, food retailers and even the public.

It should be appreciated that the exemplary system for measuring chemicals (SYS2) can be networked with other systems throughout various facilities, plants, factories, locations or areas. The data from a plurality of such systems (SYS2) can be used to predict dispersion of the chemical or unwanted condition so that preemptive action can be taken to minimize exposure or cost or streamline control system strategies.

Figure 4:
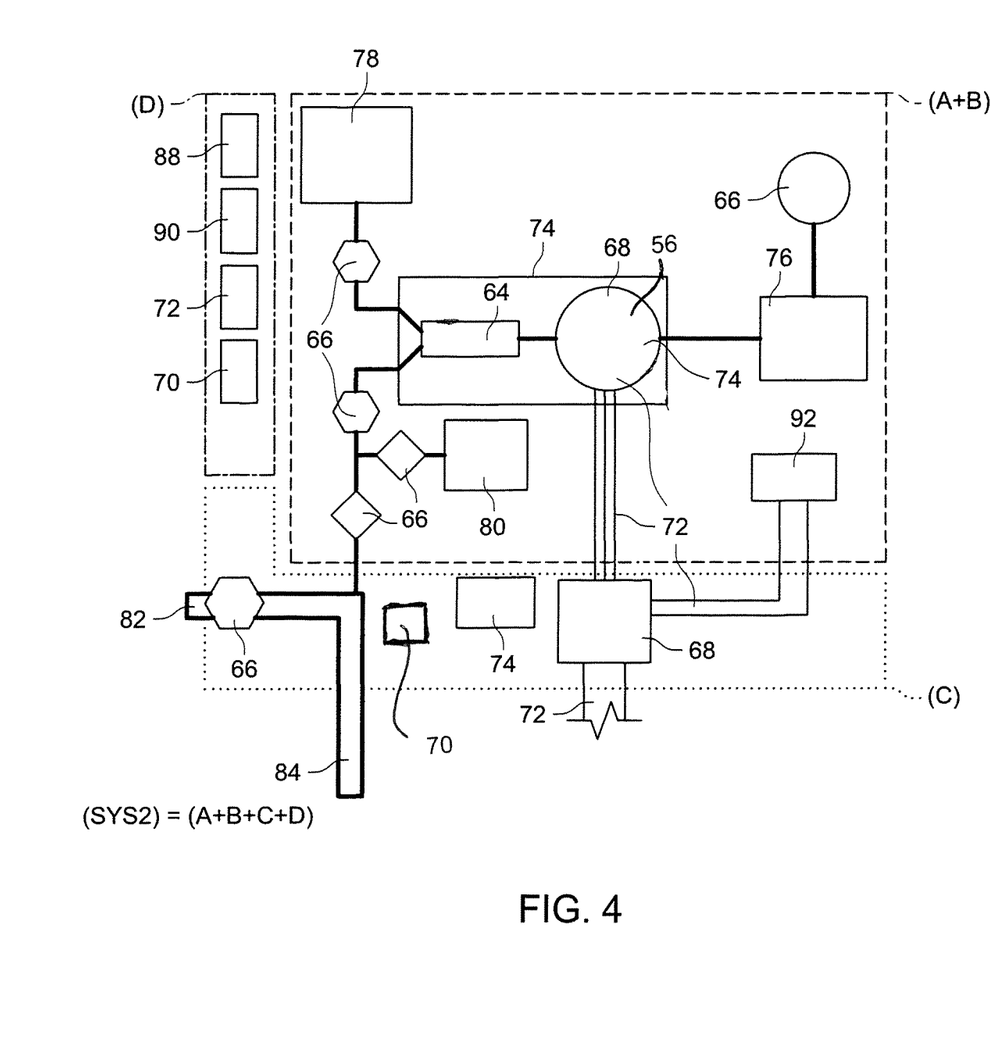
FIG. 4 illustrates an exemplary arrangement of components or elements of the second exemplary system in accordance with the present disclosure.

In FIG. 4, an exemplary arrangement of components or elements for the second exemplary system for measuring chemicals and other factors (SYS2) is presented, including the system for chemical detection (A+B), the durable transmitter (C) and the receiver (D). All components (A+B+C+D) make-up the second exemplary system for measuring chemicals or attributes or characteristics (SYS2).

The system for measuring chemicals (A+B) can be connected to the transmitter (C) through active or passive induction devices or components (66) in the form of a flow conduits, connectors, valves, pumps etc. The valve along with other active or passive induction devices or components (66) in the form of pumps regulate flow, pressure and other factors of the process matter to the mixer (64) where the process matter can be mixed with at least one other form of matter such as calibration or diluent matter from the diluent reservoir (78). Such diluents can include ionized or distilled water or buffer solutions among other types of diluents or calibration fluids or gases. The detector/sensor (56) can detect, measure or monitor the matter in the mixer (64). The system (A+B) can also be connected to the transmitter (C) that moves measurement data from the detector/sensor components (56) to measurement hardware (68) of the transmitter (C). The connection between the system (A+B) and the transmitter (C) can be wireless or through a wired connection.

Note that in FIG. 4 diamonds represent exemplary induction devices such as valves, pentagons represent pumps and thick lines represent tubes or flow conduits; all of which are considered devices or components for active induction as set forth in the present disclosure. While the exemplary rectangles, squares and circles represent other types of system components and thin lines represent electronic connection through wires or wireless. Also the various types of dotted lines correspond to the major system components (e.g. A+B, C or D). Some of these connotations are also used in FIG. 3.

The second exemplary system (SYS2) further comprising of measurement hardware (68) that can be in the form of a potentiostat among other sensor measurement hardware. The hardware is coupled to an active/passive power sources (70) that can include a photovoltaic cell, solar cell, antenna or other types of power sources. The measurement hardware also relates to communication circuitry (72) that can be in the form of wired or wireless telemetry. Factor controls (74) such as thermistors, pH balancers, humidity controls or temperature controls etc. can be used to better manage the substance and flow of materials based on temperature, pH level, humidity and various other factors that affect operability of the detectors/sensors (56).

Figure 5:
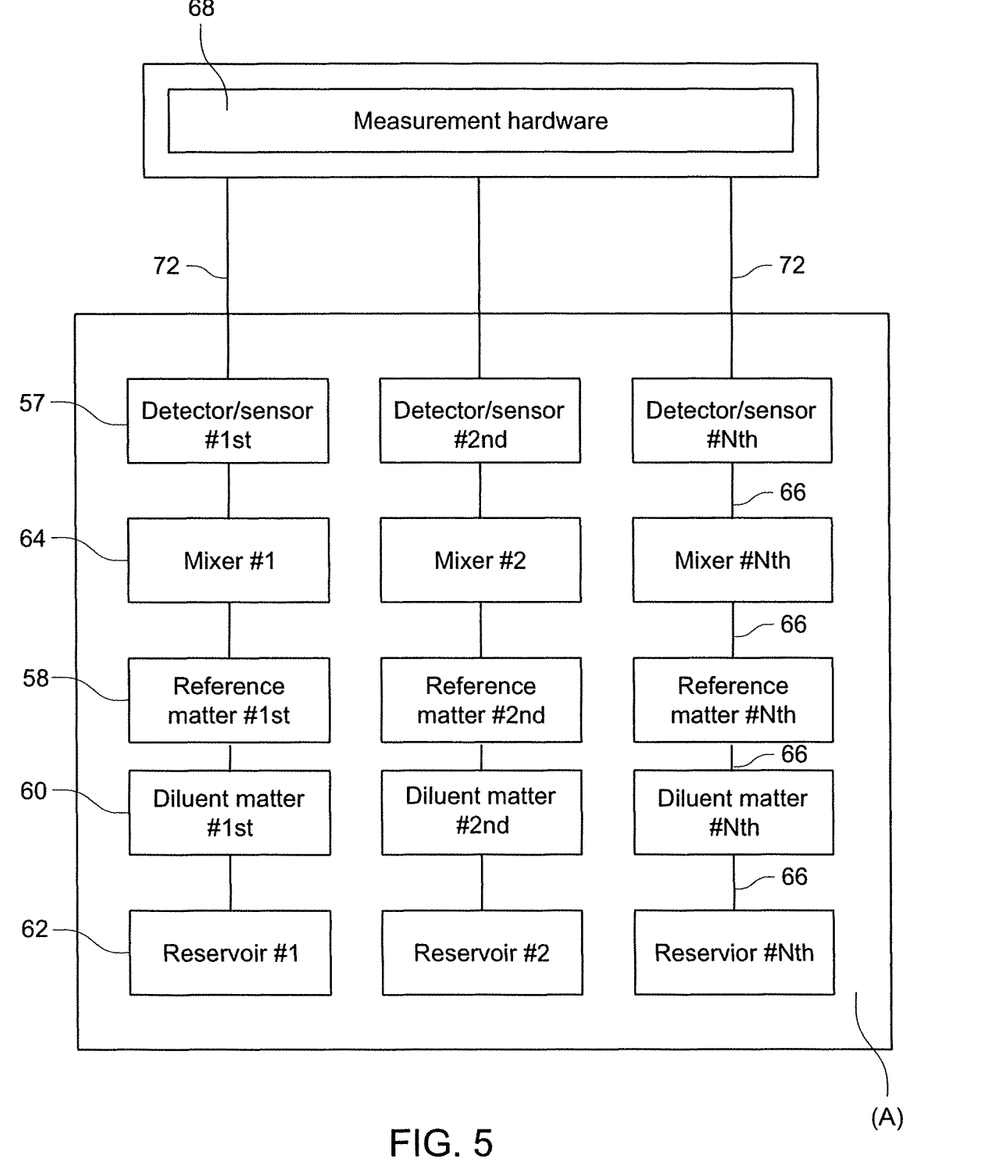
FIG. 5 illustrates a schematic diagram of an exemplary removeable/replaceable cartridge in accordance with the present disclosure.

Detectors/sensors can be calibrated using various reference matter (58) (e.g. solid, liquid or gas) stored in reservoirs (62) of the removable/replaceable cartridge (A) or other components of the system (SYS2). Active inductors (66) can be used to regulate the flow of matter from various reservoirs to the mixers (64) or throughout the system. The calibration data is stored in the calibration ID (92) and is referred to when producing measurement data associated with various test matter. After measurements of various test matter are made, the test matter is moved into a waste reservoir (76) that has an active/passive induction devices or component (66) that can be in the form of a hydrophobic vent. The hydrophobic vent is shown in FIG. 5 as a circle connected to the waste reservoir (76).

It should be appreciated that various embodiments of the second exemplary system (SYS2) allow for sensor calibration using the reference matter and measurement of the process matter to occur at different time or even simultaneously using at least two sets of system elements or components. It can also be the case that the same sensor (68) can have more than one calibration for the same process matter or more than one calibration across multiple forms of matter. Furthermore, calibrations can be estimated based on at least one or a series of previous calibrations.

In another embodiment, sensors are calibrated with a maximum and minimum linear range using a process solution and reference solution. For example, when measuring a chemical concentration of matter with a maximum measurement of 80, the reference solution and process solution is diluted by the same factor of 40. We know the post-diluted reference solution should measure at 2 and if the post-diluted process solution also measures at 2, then we know that the pre-diluted concentration of the process solution is also 80. However, if the post-diluted process solution measures at 1, then we know the pre-diluted process solution measured at 40.

The transmitter (C) can contain an inlet (82) where the sample matter enters the second exemplary system (SYS2). An active induction device/component (66) in the form of a pump is used to regulate, filter, pressurize and flow process matter to the mixer (64) and other system components. Imbedded in the pumping mechanism or separate from the pumping mechanism can be a filter in the form of a nanoporous membrane or other suitable filter used to filter out tiny biomolecules, micromolecules, macromolecules or other sized particles. Such filters can also be used throughout the system where desired and are considered active/passive induction devices/components (66). The filtered materials are discarded using other active inductions such as a purge (84).

Other components of the transmitter (C), can include factor controls (74), that can be in the form of a humidity control, temperature control, pH control or peltier used for thermoelectric heating/cooling among other control components or elements. The measurement hardware (68) is coupled to active/passive power sources (70) that can include a photovoltaic cell, solar cell, antenna or other type of power sources. The measurement hardware (68) is also coupled to communication circuitry (72) for transmitting data in wireless or wired telemetry form. ID calibration (92) relates to the measurement hardware (68) of the transmitter (C) through a wired/wireless connection. Reference measurements and calibration curves are stored in the ID calibration (92) and referred to during the measurement process.

The receiver (D) can be in the form of a remote terminal, computer, personal communication device, distributed control system (DCS) or other peripheral devices. It can include: a processor (88), memory (90) and communication circuitry (72) that is coupled to an active/passive power sources (70) that can be in the form of a photovoltaic cell, solar cell, antenna or other type of power source.

FIG. 5 provides a schematic diagram of an exemplary removable/replaceable cartridge (A) in accordance with the present disclosure. The diagram shows that the sensor component (56) or sensors (57) relate with the measurement hardware (68) through communication circuitry (72) in the form of a wired electrical or wireless telemetry connection. The reference matter (58) and diluent matter (60) are pumped to the mixer (64) where the matters are uniformly combined and prepared for measurement by the sensor (57). After the matters are measured, they are pumped to the waste reservoirs (62).

It should be appreciated that the removable/replaceable cartridge (A) can contain various active/passive induction devices/components (66) such as conduits, connectors, compressors, concentrators, fans, filters, pumps, vents, valves, channels, coatings among other flow inducement or flow regulation or pressure regulation mechanisms as need and as specified in FIG. 3. It is also appreciated that the cartridge (A) can be designed to contain any number of sensor component (56) or sensors (57), reference matter (58) diluent matter (60) and reservoirs (62) for storing matter.

Figure 6A:
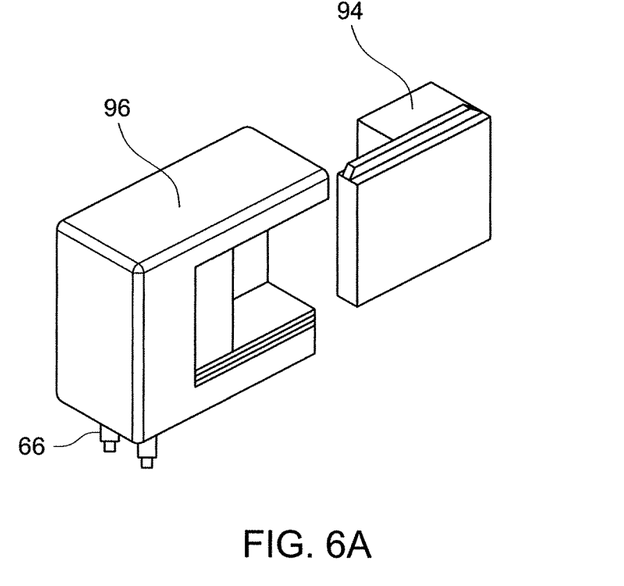
FIG. 6A illustrates a first perspective view of an exemplary removeable/replaceable cartridge.
Figure 6B:
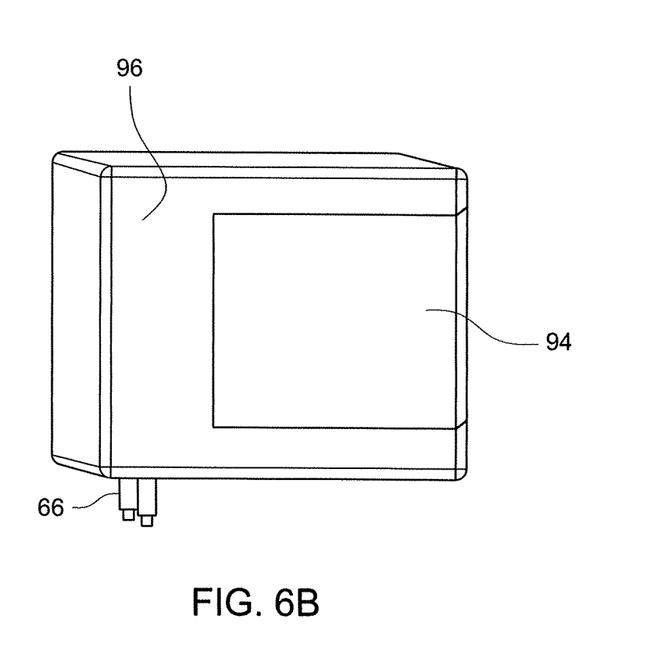
FIG. 6B illustrates a second perspective view of an exemplary removeable/replaceable cartridge.

FIGS. 6A-6B illustrate exemplary perspectives the removable/replaceable cartridge (A). FIG. 6A illustrates an exemplary removable/replaceable portion of the cartridge (94) connecting or mating with another exemplary portion of the cartridge (96). FIG. 6B illustrates the cartridge (A) connecting with the second exemplary system (SYS2) through induction devices or components (66) in the form of a connector.

It should be appreciated that in certain embodiments the second exemplary system (SYS2) can include more than one cartridge of various sizes and shapes or no cartridge at all. It should also be appreciated that various embodiments can have different types of cartridge designs. For example, in one embodiment a cartridge is not be used, but instead larger containers or reservoirs of matter are used, while the sensors can be replaced through a different mechanism.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A system for detecting, measuring or monitoring one or more factors in an environment, the system comprising:
a sensor having a detector component
a mixer;
a reference matter;
a diluent matter;
a first measurement hardware;
a first communication circuitry;
a controller;
a first container;
a second container;
a third container;
a first factor control;
one or more active induction components or one or more passive induction components; and
a first power source wherein the first power source is operatively coupled to and is configured to supply power to at least one of the detector component, the first factor control, the first measurement hardware, the mixer and the communication circuitry, wherein the communication circuitry is configured to transmit a set of data to at least one of a transmitter and a receiver wherein the system is operative to generate the set of data indicative of at least one of one or more analytes in the environment and of the one or more factors in the environment and to communicate the set of data to the transmitter or the receiver; wherein the first measurement hardware contains the detector component and wherein the controller is configured to calibrate said detector component by i) establishing a baseline measurement value of a known reference matter, ii) diluting the reference matter by a first amount and iii) diluting a process matter by a second amount wherein the second amount equals the first amount so as to generate a measurement value for the process matter; and wherein the reference matter is stored in the first container, the diluent matter is stored in the second container and the third container is configured to store a waste or a process matter, and wherein at least the first container is coupled to the mixer and to first measurement hardware through one of the one or more active induction components or through one of the one or more passive induction components, or at least the second container is coupled to the mixer and to the first measurement hardware through one of the one or more the active induction components or through one of the one or more passive induction components, or at least the third container is coupled to the mixer and to the first measurement hardware through one of the one or more active induction components or through one of the one or more passive induction components.

2. The system of claim 1, wherein the transmitter includes at least one of a first inlet, a purge, a second factor control, a second measurement hardware, said first power source, a second communication circuitry, and wherein the second communication circuitry is configured to transmit data to the receiver;
wherein the receiver includes at least one of a processor, a memory, a second power source or a third communication circuitry; and
wherein the controller comprises an induction device comprising
a first case;
a coating;
a compressor;
a connector;
a concentrator;
a conduit;
a channel;
a fan;
a filter;
a first housing;
a second inlet;
a louver;
a micro-pumps;
a pressure fitting;
a pump;
a purge;
a vacuum;
a valve;
a vent; and
a seal.

3. The system of claim 1, wherein said factor control includes a controlling device for controlling at least one of a temperature, a humidity, a pH, an amount of light, a viscosity, a flow, an aeration, an acetate concentration, an oxygenation level, or a chemical concentration.

4. The system of claim 1, wherein at least one of the detector component, the mixer, the first factor control, the first communication circuitry, the first measurement hardware or the first power source includes a printed element.

5. The system of claim 1, wherein the system is selectively attachable to a system component of at least one of a chemical processing system, a distribution system, a storage system or a transportation system, said system component having an interior chamber for transmitting or storing a solid, a liquid or a gas, and wherein the system is located in an interior portion of the interior chamber wherein the interior chamber, is configured to contain a solid, a liquid or a gas.

6. The system of claim 5, wherein the system component includes a tank or a fourth container.

7. The system of claim 6, wherein the chemical processing system, the distribution system, the storage system or the transportation system is stationary within the system component; or the chemical processing system, the distribution system, the storage system or the transportation system is mobile within the system component or the chemical processing system, the distribution system, the storage system or the transportation system is tethered to the system component such that the chemical processing system, the distribution system, the storage system or the transportation system has a limited range of motion or the chemical processing system, the distribution system, the storage system or the transportation system has a density equal to or less than a density of a matter being monitored or measured within the system component.

8. The system of claim 1, wherein the first power source includes an antenna configured to receive energy wirelessly and directly supply the received energy to at least one of the detector component, the first factor control, the first measurement hardware, the controller, or the first communication circuitry.

9. The system of claim 2, wherein the system includes a second housing or a second case that is selectively attachable to the receiver.

10. The system of claim 2, wherein the receiver includes at least one of a personal communication device or an electronic device or a peripheral device or a wearable receiver or an implantable receiver or a textile receiver or a remote receiver or a distributed control system.

11. The system of claim 2, wherein the receiver includes a non-transitory computer readable medium storing instruction for causing the processor to execute an application for processing the data, the application configured to: receive a set of data or a set of information form the monitoring device; and analyze the set of data to detect or measure or monitor one of more analyte concentrations or one or more factors in the environment.

12. A method for detecting or measuring or monitoring one or more analytes or one or more factors in matter using the system of claim 1, the method comprising:
associating said sensor with a location within an area to be measured or monitored;
measuring or monitoring the location with said sensor over a period of time;
transmitting data generated by the sensor to a receiver;
calibrating said detector component with said controller by using said reference matter, said process matter and said diluent matter by establishing a baseline measurement for a known reference matter; and
diluting at least said reference matter by a first amount or at least said process matter by a second amount to a predetermined chemical concentration to generate a measurement value for said process matter wherein the first amount equals the second amount.

13. The method of claim 12, wherein said controller further comprises an induction device or a directing component for actively or for passively directing a flowable substance towards or away from the detector component.

14. The method of claim 12, wherein the factor control includes an element for controlling a temperature, a humidity, a pH, an amount of light, a viscosity, a flow, an aeration, an acetate concentration, an oxygenation level, or a chemical concentration.

15. The method of claim 12, wherein the predetermined chemical concentration is between a minimum concentration and a maximum concentration of a measurable concentration to be measured.

16. The method of claim 15, further comprising:
diluting the reference matter by a first predetermined amount;
diluting the process matter by a second predetermined amount wherein the first predetermined amount equals the second predetermined amount; performing a calculation to generate concentration of the pre-diluted process matter.

* * * * *